United States Patent
Lang et al.

(10) Patent No.: US 6,933,337 B2
(45) Date of Patent: Aug. 23, 2005

(54) PLASTISOL COMPOSITIONS COMPRISING VINYL CHLORIDE POLYMERS AND MIXTURES OF AROMATIC AND ALIPHATIC ESTERS OF DIOLS AS PLASTICIZERS

(76) Inventors: Jiamin Lang, 510 E. Knob Hill Dr., Arlington Heights, IL (US) 60004; Bruce Edward Stanhope, 879 N. Alleghany, Grayslake, IL (US) 60030; Thomas Joseph Bohnert, 100 Meaderboro Rd., Rochester, NH (US) 03867; William David Arendt, 417 Catalpa La., Libertyville, IL (US) 60048

( * ) Notice: Subject to any disclaimer, the term of this patent is extended or adjusted under 35 U.S.C. 154(b) by 0 days.

(21) Appl. No.: 10/393,214

(22) Filed: Mar. 20, 2003

(65) Prior Publication Data

US 2003/0181556 A1 Sep. 25, 2003

Related U.S. Application Data

(63) Continuation-in-part of application No. 09/832,554, filed on Apr. 11, 2001, now abandoned.

(51) Int. Cl.$^7$ .................................................. C08K 5/09
(52) U.S. Cl. ..................... 524/290; 524/291; 524/292; 524/306; 524/308; 524/310
(58) Field of Search ................................. 524/290, 291, 524/292, 306, 308, 310

(56) References Cited

U.S. PATENT DOCUMENTS

| 2,585,448 | A |   | 2/1952 | Emerson et al. ............ 260/31.6 |
| 2,637,714 | A |   | 5/1953 | Emerson et al. ............ 524/292 |
| 2,700,656 | A |   | 1/1955 | Emerson et al. ............ 524/293 |
| 3,046,237 | A | * | 7/1962 | Rosenfelder et al. ....... 524/114 |
| 3,072,591 | A |   | 1/1963 | Fath ............................ 524/287 |
| 3,370,032 | A |   | 2/1968 | Potter ......................... 260/31.6 |
| 3,736,348 | A |   | 5/1973 | Gough et al. ............ 260/475 R |
| 3,785,977 | A |   | 1/1974 | Flowarday et al. ......... 252/33.6 |
| 3,939,201 | A | * | 2/1976 | Bacskai ....................... 560/263 |
| 4,981,889 | A | * | 1/1991 | Baba et al. .................. 524/109 |
| 5,006,585 | A | * | 4/1991 | DiBella ....................... 524/293 |
| 5,177,135 | A | * | 1/1993 | Wehner et al. .............. 524/315 |
| 5,319,028 | A | * | 6/1994 | Nakamura et al. .......... 525/227 |
| 5,739,203 | A | * | 4/1998 | Ngoc .......................... 524/527 |
| 6,531,533 | B1 | * | 3/2003 | Kuhn et al. ................. 524/450 |

FOREIGN PATENT DOCUMENTS

| GB | 715995 A | 9/1954 |
| WO | WO 01/00722 A1 | 1/2001 |

OTHER PUBLICATIONS

A. V. Bailey, G. J. Boudreaux, and G. Sumrell, "*Preparation of Some Mixed Diesters of Aliphatic Diols and Their Evaluation as Plasticizers*", Journal of the American Oil Chemists' Society, vol. 53 pp. 176–178, May, 1976.

PCT Search Report, Application No. PCT/US02/10907, Applicant: Velsicol Chemical Corporation, Jul. 18, 2002 (6 pages).

* cited by examiner

*Primary Examiner*—Bernard Lipman
(74) *Attorney, Agent, or Firm*—Fitch, Even, Tabin & Flannery

(57) ABSTRACT

Mixtures of esters produced by reacting a mixture of aromatic and aliphatic monocarboxylic acids with a diol containing from 2 to 12 carbon atoms are effective plasticizers for plastisols containing dispersion grade polymers of vinyl chloride. The freezing point of the present ester mixtures and their efficacy as plasticizers can be varied by adjusting the type and relative concentration of the aliphatic acid used to prepare the plasticizer. The ester mixtures can also be used as plasticizers for other organic polymers.

5 Claims, No Drawings

PLASTISOL COMPOSITIONS COMPRISING VINYL CHLORIDE POLYMERS AND MIXTURES OF AROMATIC AND ALIPHATIC ESTERS OF DIOLS AS PLASTICIZERS

RELATED APPLICATIONS

This application is a continuation-in-part of application Ser. No. 09/832,554, filed Apr. 11, 2001 now abandoned.

BACKGROUND OF THE INVENTION

1. Field of the Invention

This invention relates to novel plasticized polymer compositions. More particularly, this invention relates to plastisol compositions comprising 1) a dispersion grade of a homopolymer or copolymer of vinyl chloride and 2) as the plasticizer, a mixture comprising a) the diester derived from a diol containing from 2 to 12 carbon atoms and an aromatic monocarboxylic acid, b) the diester derived from said diol and an aliphatic monocarboxylic acid and c) a mixed ester of said diol and said aromatic and aliphatic monocarboxylic acids. The aromatic monocarboxylic acid is benzoic acid or a substituted benzoic acid. Small concentrations of the monoesters of either or both of the monocarboxylic acids can also be present.

This invention also relates to plasticized polymer compositions containing the plasticizers of this invention in combination with organic polymers other than polyvinyl chloride.

Preferred plasticizers of this invention are low viscosity liquids at 25° C. and are effective primary plasticizers for plastisols containing vinyl chloride polymers.

2. The Prior Art

Ester compositions prepared by reacting a diol with a mixture of benzoic acid and an alkanoic acid and the use of these ester compositions as plasticizers for vinyl chloride polymers that are fabricated as molten materials is taught in a number of patents, including U.S. Pat. Nos. 2,585,448, 2,637,714 and 2,700,656 to Emerson and Longley.

Homopolymers and copolymers of vinyl chloride are available in two forms that are defined by both average size of the polymer particles and behavior of the polymer in the presence of a plasticizer. One form, which is described in the aforementioned prior art, is referred to as a "general purpose" or "suspension grade" polymer. When this type of polymer is combined with a liquid plasticizer, the plasticizer is absorbed into the interior portion of the polymer particles and the product is a dry powder at 25° C. The polymer can prepared by suspension polymerization, and typically exhibits an average particle size of 150 microns. The plasticized polymer is typically fabricated by heating the particulate form of the polymer to form a molten material using techniques including, but not limited to, hot roll milling, extrusion, injection molding and calendaring. All of the vinyl chloride polymers described in the aforementioned patents to Emerson et al. are suspension grade polymers.

A second type of vinyl chloride polymer is used in the preparation of plastisols. This type of polymer exhibits an average particle size of less than 10 microns. Emulsion polymerization is one technique for preparing this type of polymer. When this form of polymer, often referred to as a dispersion grade polymer, is treated with a liquid plasticizer, the plasticizer remains exterior to the polymer particles and the resultant liquid/solid suspensions are referred to as plastisols. The flow characteristics exhibited by these plastisols range from those of liquids to non-drip paints.

End use applications for plastisols include but are not limited to coatings and films. Following application of the plastisol to a substrate, the plastisol is heated to melt the suspended polymer particles and fuse them together to form a unitary article.

Particle size can be measured using known techniques including, but not limited to, microscopic examination of the particles and the use of a series of sieves of gradually decreasing mesh size.

In summary, suspension and dispersion grades of vinyl chloride polymers are characterized and distinguished from one another both by their average particle size and their behavior in the presence of a liquid plasticizer.

U.S. Pat. No. 3,370,032 to Potter discloses a plasticizer for vinyl chloride plastisols. The plasticizer is obtained by reacting 1) a dihydroxyl-substituted ester derived from 2-hydroxymethyl-2-methylpropanoic acid and 2-hydroxymethyl-2-methylpropanol with 2) a mixture of aliphatic and aromatic carboxylic acids. The aromatic acid constitutes from 30 to 70 weight percent of the acid mixture used to prepare the plasticizer.

In accordance with the teaching of this patent, the advantage of using the diester of the mixed aromatic/aliphatic acids in place of the corresponding dialiphatic acid ester is the higher solvating ability of the mixed ester for the vinyl chloride polymer, resulting in a lower "flux temperature" exhibited plastisols containing the mixed benzoate/alkanoate ester as a plasticizer relative to the flux temperature of plastisols containing the dibenzoate. The patent defines "flux temperature" as the minimum temperature to which the mixture of polymer and plasticizer must be heated to allow the particles of plasticizer suspended in the plastisol to fuse to form a unitary solid material such as a film.

The present invention resides in the discovery that some of the mixed ester plasticizers disclosed in the aforementioned patents to Emerson and Longly, which are taught as being useful only for suspension grade vinyl chloride polymers, can be substituted for the structurally unrelated ester compositions of the Potter patent in plastisols. The resultant plastisols exhibit unexpected advantages that include but are not limited to relatively low freezing point of the plasticizer and low viscosity of the plastisol in the absence of excessive softness in shaped articles such as films and coatings prepared using the plastisol. These advantages are unexpected based on the lack of specific or implied teachings concerning these advantages in any of the aforementioned Potter or Emerson et al. patents.

When used at levels that achieve the desired reduction in plastisol viscosity, many prior art plasticizers excessively soften shaped articles prepared from the plasticizer. A commonly used method for avoiding this excessive softening is to reduce the concentration of plasticizer and include a volatile organic solvent that, like the plasticizer, reduces the viscosity of the plastisol, thereby facilitating processing of the plastisol, but is volatilized or otherwise removed during fusing of the polymer particles in the plastisol to form a shaped article. The recovered diluent must be recovered for reuse or disposed of in an environmentally acceptable manner.

DETAILED DESCRIPTION OF THE INVENTION

The plastisol compositions of this invention comprise:
A) particles of a dispersion grade polymer selected from the group consisting of homopolymers and copolymers of vinyl chloride, wherein the average size of said particles is less than 10 microns; and B) from 10 to 100 weight percent, based on the weight of said polymer, of a plasticizer composition comprising
1) an ester corresponding to formula (I)

$$R^1C(O)OR^2O(O)CR^3; \quad \text{I}$$

2) an ester corresponding to formula (II)

$$R^1C(O)OR^2O(O)CR^1; \text{ and} \quad \text{II}$$

3) an ester corresponding to formula (III)

$$R^3C(O)OR^2O(O)CR^3 \quad \text{III}$$

wherein $R^1$ is at least one radical selected from the group consisting of phenyl and alkyl-substituted phenyl, $R^2$ is a divalent radical of the formula $—R^4(OR^4)_m—$, $R^3$ is an alkyl radical containing from 3 to 21 carbon atoms, $R^4$ is an alkyl radical containing from 2 to 4 carbon atoms, $\underline{m}$ represents 0 or the integer 1 or 2 and the molar ratio of $R^1$ to $R^3$ radicals is from 1:2 to 15:1.

The present ester compositions are prepared by reacting a diol of the formula $HOR^2OH$ with a mixture of 1) an aromatic monocarboxylic acid of the formula $R^1C(O)OH$ and 2) an aliphatic monocarboxylic acid of the formula $R^3C(O)OH$. The total moles of said aromatic and aliphatic carboxylic acids in the initial reaction mixture are equal to at least twice the number of moles of said diol and $R^1$, $R^2$ and $R^3$ are as hereinbefore defined.

In preferred embodiments of the present ester compositions, the molar ratio of $R^1C(O)—$ to $R^3C(O)—$ groups in said composition is at least 1:1, $R^1$ is phenyl, $R^3$ contains from 8 to 16 carbon atoms, $\underline{m}$ is 1 or 2, and the composition is a liquid at 25° C. Most preferably $R^4$ is ethyl or propyl, the molar ratio of $R^1C(O)—$ to $R^3C(O)—$ groups in said composition is from 3:1 to 12:1, and $R^3$ contains 11 carbon atoms.

The plasticizer portion of the present plastisols can optionally contain up to about 5 percent by weight of monoesters of the diol $HOR^2OH$ and the aromatic and/or aliphatic carboxylic acids used to prepare the ester. These monoesters are represented in this specification by the formulae $R^1C(O)OR^2OH$ and $R^3C(O)OR^2OH$, wherein $R^1$, $R^2$ and $R^3$ are as previously defined. The presence of these monoesters should be minimized because the monoesters usually increase the volatility of the ester composition. Volatility of a plasticizer is typically undesirable because the resultant loss of plasticizer typically causes the viscosity of the plastisol to gradually increase with time.

The total plasticizer concentration in a plastisol of the present invention can include other known plasticizers in addition to the mixed esters described in this specification. Known plasticizers include but are not limited to benzoic acid esters of monohydric alcohols in addition to phthalates and adipates derived from monohydric alcohols.

This invention also provides plasticized polymer compositions containing an ester composition of the present invention as a plasticizer in combination with a polymer that is either a thermoplastic polymer selected from the group consisting of cellulose ester polymers, polystyrene, and chlorinated polyethylenes or an elastomeric polymer selected from the group consisting of polyacrylates, acrylic copolymers, homopolymers and copolymers of vinyl acetate, styrene/butadiene copolymers, polysulfides and natural rubber. The plasticizer constitutes up to 70 percent of the combined weight of said ester composition and the thermoplastic or elastomeric polymer. The optimum range of plasticizer concentration will vary with the particular polymer selected and can readily be determined with a minimum of experimentation.

As previously disclosed for plastisols, the total plasticizer can include other known plasticizers in addition to the mixed esters of the present invention. Known plasticizers include but are not limited to benzoic acid esters of monohydric alcohols in addition to phthalates and adipates derived from monohydric alcohols.

An unexpected advantage of the present ester compositions is that by selecting preferred ranges for 1) the molar ratio of the aromatic monocarboxylic acid to the aliphatic monocarboxylic acid and 2) the number of carbon atoms in the aliphatic carboxylic acid, the physical properties such as melting point, viscosity and volatility exhibited by the resultant mixture of esters and the compatibility of these mixtures in plastisols containing vinyl chloride polymers can be varied over a wide range to achieve a desired combination of properties. Preferred ester compositions and the molar ratio of aromatic to aliphatic carboxylic acids used to prepare them are described in subsequent sections of this specification.

Because carboxylic acids typically react at different rates, the relative concentrations of the three diesters that can be formed are difficult to predict. The distribution of reaction products is influenced by 1) the relative concentrations of aromatic and aliphatic carboxylic acids in the initial reaction mixture, 2) the temperature of the reaction mixture and 3) the total reaction time.

The accompanying examples demonstrate that a reaction mixture containing a 6:1 molar ratio of benzoic acid to the aliphatic carboxylic acid will produce an ester mixture containing a higher concentration of dibenzoate and a lower concentration of the mixed benzoate/alkanoate ester than a reaction mixture in which this molar ratio is 1:1.

The difficulty of precisely predicting the relative concentrations of the possible mono- and diesters in the present ester mixtures from the molar ratio of the two carboxylic acids used to prepare them does not affect the utility of the present mixtures as primary plasticizers for plastisols containing polyvinyl chloride and for other organic polymers.

Preparation of the Mixed Esters

The mixed ester compositions of this invention can be prepared by reacting the desired diol with a substantially equimolar quantity of a mixture consisting essentially of 1) an aromatic carboxylic acid selected from the group consisting of benzoic acid and substituted benzoic acids and 2) an aliphatic monocarboxylic acid containing from 3 to 22 carbon atoms. Substituted benzoic acids such as toluic acid can be used in place of benzoic acid. It will be understood by those skilled in the art of ester preparation that derivatives of the aromatic and aliphatic carboxylic acids, such as the corresponding acyl halides and acid anhydrides, can be substituted for the acid.

While the molar ratio of the aromatic to the aliphatic carboxylic acid and the particular aromatic and aliphatic acids used to prepare the initial reaction mixture are not critical with respect to operability of the process used to prepare the present compositions, the molar ratio is preferably from 1 to 12 moles of the aromatic monocarboxylic acid per mole of the aliphatic monocarboxylic acid, the aromatic carboxylic acid is preferably benzoic acid and the aliphatic carboxylic acid preferably contains from 9 to 17 carbon atoms. These preferences are based on the properties, particularly melting point and volatility, of the resultant ester mixtures, the efficacy of the ester compositions as plasticizers for plastisols containing vinyl chloride polymers, and the properties of the articles prepared using the plastisols.

Diols suitable for use in preparing the ester compositions of the present invention can be represented by the general formula HOR⁴(OR⁴)$_m$OH. In this formula R⁴ represents an alkyl radical containing from 2 to 4 carbon atoms, and m represents 0 or the integer 1 or 2.

Preferred diols include but are not limited to ethylene glycol, propylene glycol, 1,3-propanediol, 2-methyl-1,3-propanediol, diethylene glycol, dipropylene glycol, triethylene glycol, 1,3-butanediol and 1,4-butanediol. Diols wherein R⁴ is ethyl or n-propyl and m is 1 or 2 are particularly preferred based on their cost and commercial availability.

Because esterification is typically a reversible reaction, this reaction is typically conducted at the boiling point of the reaction mixture and the water produced as a by-product of the reaction is preferably distilled from the reaction mixture and collected. To increase the rate of the esterification reaction, it is preferably conducted in the presence of a suitable catalyst such as a mineral acid, an organotin compound, an organotitanium compound and/or a zirconium compound. Suitable catalysts include but are not limited to the organic sulfonic acids such as toluene sulfonic acid, tin compounds such as stannous octoate, tetrabutyl titanate and zirconium carbonate. These catalysts can be used alone or in combinations of two or more.

The procedures and equipment used to prepare, isolate and analyze the ester mixtures produced from the esterification reaction are sufficiently well known to those skilled in this art that a detailed discussion is not required as part of the present specification. Gas chromatography is a preferred method for determining the types and relative concentrations of the esters in the present compositions.

To minimize the concentration of monoesters in the final ester mixture, the total moles of aromatic and aliphatic acids used to prepare the esters should be equal to twice the number of moles of diol. The concentration of monoesters can be further reduced by washing the ester mixture with an aqueous solution of a base such as potassium hydroxide.

When equal numbers of moles of diethylene glycol, benzoic acid and lauric acid were reacted and the resultant mixture of esters treated with aqueous potassium hydroxide solution followed by washings with water to reduce the concentration of monoesters, analysis of the product using gas chromatography showed the mixture to contain less than 0.5 percent diethylene glycol monobenzoate, 4 percent diethylene glycol monolaurate, 14 percent diethylene glycol dibenzoate, 45 percent diethylene glycol monobenzoate monolaurate and 36 percent diethylene glycol dilaurate, based on the relative areas of the peaks on the output chart of the chromatograph.

Properties of Preferred Mixed Esters

Ester mixtures prepared by reacting benzoic acid and a carboxylic acid containing from 9 to about 17 carbon atoms with one of the present diols are preferred based on their unexpected combination of properties that make these esters particularly useful primary plasticizers for plastisols containing organic polymers such as homopolymers and copolymers of vinyl chloride.

Data in the accompanying examples demonstrate that the viscosity and freezing point of these esters are unexpectedly low relative to the corresponding diester of benzoic acid. As the molar ratio of benzoic acid to lauric acid in the initial reaction mixture was increased from 1:1 to 9:1, the freezing point of the resultant ester mixture decreased from 25° C. to a minimum of about −15° C. As this molar ratio increases beyond 9:1 to the absence of the aliphatic carboxylic acid, the freezing point of the resultant ester mixture increases to about 25° C. for diethylene glycol dibenzoate.

Performance of the Present Mixed Esters as Plasticizers

Mixed esters prepared from benzoic acid, an aliphatic carboxylic acid containing from 8 to 16 carbon atoms and a diol such as diethylene glycol are particularly useful plasticizers based on the unique combination of an unexpectedly low freezing point and low volatility of the mixed ester and the low viscosity and relatively low gel temperature of the plastisol. Gel temperature is the only property disclosed in the aforementioned U.S. Pat. No. 3,370,032 issued to Potter. This patent discloses only one mixed ester plasticizer based on a partially esterified diol that is not structurally related to the diol portion of the present mixed diesters. More significantly, this patent does not suggest that mixed esters of the disclosed diol exhibit the unexpectedly low plasticizer volatility and freezing point and low plastisol viscosity that characterize the present plasticizers.

The following examples describe preferred embodiments of the present ester mixtures, a preferred method for preparing them, the physical properties of these mixtures and the properties of polyvinyl chloride plastisols containing these mixtures as plasticizers. The examples should not be interpreted as limiting the scope of the invention defined in the accompanying claims. Unless otherwise specified, all parts and percentages in the examples are by weight and the physical properties of the esters mixtures were measured at 25° C.

EXAMPLE 1

Four mixed ester compositions of the present invention were prepared by charging a glass reactor with diethylene glycol (OHCH$_2$CH$_2$OCH$_2$CH$_2$OH) as the diol, benzoic acid as the aromatic carboxylic acid, lauric acid as the aliphatic carboxylic acid, and, as the catalyst for the esterification reaction, 0.1 percent, based on the weight of total reactants, of a catalyst mixture containing 75 weight percent zirconium carbonate and 25 weight percent stannous oxalate. The molar ratios of benzoic to lauric acids present in the four initial reaction mixtures are listed in Table 1. The molar ratio of total carboxylic acids to glycol was 2:1 in all of these reaction mixtures.

The reactor was equipped with a thermometer to measure the temperature of the reaction mixture, a mechanically driven stirrer, an inlet for nitrogen extending below the surface of the reaction mixture, and a trap to collect the vaporized water formed as a by-product of the esterification reaction. A water-cooled reflux condenser was located above the trap to liquefy the water and other vaporized materials.

The contents of the reactor were gradually heated to liquefy the solid reactants and initiate vaporization of volatile materials. At a reaction mixture temperature of about 180° C. all of the initial reactants had liquefied and liquid had begun to vaporize and collect in the trap. The boiling point of the reaction mixture gradually increased to 250° C. Following about 4 hours of heating, the acid number of the reaction mixture was measured at 30-minute intervals until a value of 5 or less was measured. A small volume of diethylene glycol was added if the acid number remained above 5 and did not change between successive samplings.

When the acid number of the reaction mixture had decreased to 5 or less, heating of the reaction mixture was discontinued and the mixture was allowed to cool to 90° C. At this time, a volume of a 10 weight percent aqueous potassium hydroxide solution equal to about ⅓ the volume of the reaction mixture was added to the reactor. After about 15 minutes of stirring, the aqueous layer was separated and discarded. The organic layer was washed three times using volumes of 10 weight percent aqueous potassium hydroxide solution equal to that used for the first washing, followed by at least three washings with hot demonized water until the pH of the organic layer was 7.

The types and relative concentrations of esters in the reaction product, a clear, colorless liquid, were determined using a Hewlett Packard HP6890 series gas chromatograph equipped with a type HP-5 column packed with phenyldimethylpolysiloxane that was 5% cross linked. The column temperature was gradually increased from 80 to 320° C. and the rate of helium flow was 200 cc. per minute.

The chromatogram generated by passage of an ester mixture through the detector of the gas chromatograph contained four or five peaks, each corresponding to one of the component esters. The area under a given peak was considered directly proportional to the relative concentration of the corresponding ester. Under the operating conditions of the chromatograph, the esters of diethylene glycol emerged in the following order: the monobenzoate (DEGMB), the monolaurate (DEGML), the dibenzoate (DEGDB), the mixed benzoate/laurate (DEGBL) and the dilaurate (DEGDL).

The molar ratio of benzoic acid to lauric acid used for each of the four esterification reactions is recorded in Table 1, together with the percent of total peak area on the chromatogram corresponding to each of the aforementioned five possible esters. In each of the initial reaction mixtures the molar ratio of diethylene glycol to total carboxylic acids was 1:2.

The viscosities of the esters were measured at 25° C. using a stress-controlled rheometer manufactured by TA Instruments and equipped with a 4 cm-diameter cone-shaped plate.

The esters are identified in the same manner as in the preceding Table 1.

TABLE 2

| BENZOIC ACID/LAURIC ACID MOLE RATIO | FREEZING TEMPERATURE (° C.) | VISCOSITY @ 5° C. (Pa · s) |
|---|---|---|
| 1:1 (DEGBL) | 25 | (Solid) |
| 3:1 (DEG3BL) | 5 | 0.13 |
| 6:1 (DEG6BL) | −5 | 0.15 |
| 9:1 (DEG9BL) | −15 | 0.18 |
| 12:1 (DEG12BL) | −10 | 0.28 |
| DEGDB[1] | 25 (super-cooled) | 0.43 |

[1]Diethylene glycol dibenzoate (evaluated for comparative purposes and known to supercool)

The data in Table 2 demonstrate that ester compositions of the present invention prepared using molar ratios of benzoic acid to lauric acid within the preferred range of from 3:1 to 12:1 unexpectedly exhibit freezing temperatures below 25° C. and viscosities below 0.3 Pascal seconds. In addition, the composition prepared using a 9:1 molar ratio of benzoic acid to lauric acid exhibits an unexpectedly low freezing point, which increases with increasing amounts of either acid.

The volatility of the esters was determined using a model TGA2950 thermogravimetric analyzer manufactured by TA Instruments. The percentage weight change was measured

TABLE 1

| Benzoic Acid:Lauric Acid Mole Ratio[1] | DEGMB[2] % | DEGML % | DEGML % | DEGML % | DEGDL % |
|---|---|---|---|---|---|
| 1:1 (DEGBL) | <0.5 | 4 | 14 | 45 | 36 |
| 3:1 (DEG3BL) | <0.5 | <1 | 38 | 46 | 15 |
| 6:1 (DEG6BL) | <0.5 | <2 | 58 | 30 | 9 |
| 9:1 (DEG9BL) | <0.5 | <1 | 72 | 22 | 4 |
| 12:1 (DEG12BL) | <0.5 | <1 | 77 | 19 | 2 |

[1]All mole ratios refer to reactants
[2]All percentages based on total reaction product

EXAMPLE 2

This example demonstrates the relatively low freezing point, viscosity and volatility that make the present ester mixtures desirable as 1) plasticizers for plastisols containing polyvinyl chloride and 2) plasticizers for the other organic polymers described in a preceding section of this specification. The freezing points of the esters mixtures described in Example 1 that were liquid at ambient temperature were determined by exposing the ester mixtures to a mixture of ethylene glycol and water that was cooled to the desired temperature using a refrigeration unit. The temperature of the mixture containing a sample of the ester to be evaluated was initially 25° C. and was lowered in increments of 5° C. Each temperature level was maintained for 24 hours. The sample was examined at the end of each 24-hour period to determine if the initially liquid ester composition had solidified. The temperature at which solid material was first observed was reported as the freezing point of the ester mixture being evaluated and is recorded in Table 2. After being liquefied and cooled, pure diethylene glycol dibenzoate exhibits super-cooling, and solidifies at 25° C., which is below its actual melting point.

by exposing the sample to a temperature of 190° C. for 3 hours under a flow of nitrogen at a rate of 100 cc. per minute. The percent weight loss of each ester was determined at intervals of 30 minutes and the results are recorded in Table 3. Di-2-ethylhexyl phthalate (DOP) was evaluated for comparative purposes.

TABLE 3

| Time | % Weight Loss | | | | | |
|---|---|---|---|---|---|---|
| (Min.) | DEGBL | DEG3BL | DEG6BL | DEG9BL | DEGDB[1] | DOP[2] |
| 0 | 0 | 0 | 0 | 0 | 0 | 0 |
| 30 | 9.8 | 11.4 | 14.5 | 11.2 | 28.7 | 18.1 |
| 60 | 20.6 | 23.3 | 28.0 | 23.1 | 53.0 | 37.1 |
| 90 | 29.8 | 32.6 | 37.2 | 33.5 | 71.0 | 56.1 |
| 120 | 37.8 | 41.1 | 47.1 | 42.9 | 83.4 | 76.0 |
| 150 | 44.7 | 48.7 | 58.0 | 51.0 | 92.1 | 90.4 |
| 180 | 50.7 | 55.4 | 64.5 | 60.0 | 100 | 95.7 |

[1]Diethylene Glycol Dibenzoate (Comparison)
[2]Dioctyl Phthalate (Comparison)

The data in Table 3 demonstrate the unexpectedly lower volatility of DEG9BL relative to DEG6BL. DEG6BL, in turn, was more volatile than DEG3BL. This is an unexpected reversal of the observed trend toward higher values of volatility with increasing benzoic acid content.

EXAMPLE 3

This example demonstrates the utility of the mixed esters of this invention as plasticizers for plastisols containing polyvinyl chloride (PVC). Preferred esters of the present invention exhibit a unique combination of high solvating ability for the polymer with a relatively low viscosity of the plasticized polymer composition.

The ester compositions listed in the preceding Table 1 that were liquids at 25° C. were incorporated into two plastisol formulations. The plasticizer was used at levels of 30 and 55 parts by weight per 100 parts of PVC resin(s). The types and amounts of ingredients in the two formulations evaluated are recorded in Table 4.

TABLE 4

|  | Formulation | |
| --- | --- | --- |
|  | A | B |
| Ingredient | Parts | Parts |
| PVC | 100 | 60 |
| Blending Resin | 0 | 40 |
| Plasticizer | 55 | 30 |
| TXIB[1] | 3 | 6 |
| ESO[2] | 4 | 4 |
| Stabilizer[3] | 3 | 3 |

[1]2,2,4-trimethylpentane diisobutyrate
[2]Epoxidized Soybean Oil
[3]A calcium/zinc stabilizer available as Irgastab ® CZ 116 from Witco Chemical Corporation The polyvinyl chloride was a dispersion type polymer prepared by microsuspension polymerization and exhibited a weight average molecular weight of 200,000. It is available as Lacovyl® PB 1302 from Atochem.

The blending resin was a suspension type vinyl chloride homopolymer prepared by suspension polymerization, exhibited a weight average molecular weight of 140,000, and is available as Vinnolit (R) C65V from Wacker Chemie. The purpose of the blending resin was to reduce the viscosity of the plastisol.

Both the dispersion and suspension polymers were in the form of finely divided solids. The average particle size of the dispersion polymer was less than 10 microns and the average particle size of the suspension polymer was about 150 microns.

Plastisols were prepared by first blending the liquid ingredients using a high-speed mixer. The resultant mixture was cooled using an ice/water bath to prevent gelation of the composition during addition of the vinyl chloride polymer (s). Following addition of the polymer(s), the composition was stirred at a mixer speed of 1200 revolutions per minute for 10 minutes then deaerated for 30 minutes under reduced pressure with stirring.

The viscosity of the resultant deaerated plastisols A and B were measured using a stress-controlled rheometer manufactured by TA Instruments. The spindle of the instrument was equipped with a plate measuring 2 cm. in diameter. The shear rate was 10 sec.$^{-1}$ under ambient conditions.

The gelation temperatures of the plastisols were determined using the same rheometer and 2 cm.-diameter plate used to determine viscosity. In this instance, the plate was oscillated rather than rotated as in the case of the viscosity measurement. The temperature of the metal block on which the sample of plastisol rested was gradually increased until gelation of the plastisol occurred, which was evidenced by a sudden increase in the torque required to oscillate the plate.

A lower gelation temperature is associated with greater solvating ability of the plasticizer. The viscosity and gelation temperature of the plastisols evaluated are recorded in Table 5.

Plastisols corresponding to formulations A and B but using di-2-ethylhexyl phthalate (DOP) or a 1:1 weight ratio mixture of diethylene glycol dibenzoate (DEGDB) and triethylene glycol dibenzoate (TEGDB) in place of a mixed ester composition of the present invention were prepared and evaluated for comparative purposes.

The viscosity and gelation temperature of the plastisols are recorded in Table 5.

TABLE 5

| Plasticizer | Viscosity (Pa · s) | Gelation Temperature (° C.) |
| --- | --- | --- |
| DEG3BL | 1.1 | 67 |
| DEG6BL | 1.5 | 65 |
| DEG9BL | 1.6 | 65 |
| DEGDB/ TEGDB[1] | 3.5 | 63 |
| DOP[2] | 1.8 | 76 |

[1]a 1:1 weight ratio mixture of diethylene glycol dibenzoate and triethylene glycol dibenzoate used for comparative purposes
[2]Dioctyl Phthalate (used for comparative purposes)

The data in Table 5 demonstrate the unique combination of low viscosity and increased solvating ability, as evidenced by a lower gelation temperature, that distinguish preferred embodiments of the present mixed esters relative to widely used plasticizers for vinyl chloride polymers.

EXAMPLE 4

This example demonstrates the excellent compatibility of the present ester mixtures in plastisols containing polyvinyl chloride.

Coatings of all the plastisols described in the preceding Table 5 were applied to the coated side of paper sheets containing a releasable liner on one side of the sheet. The plastisols were then fused to form a unitary film with the release lined by heating the coated paper at 200° C. for 2 minutes. The resultant sheets were about 1 mm. Thick Samples measuring 1×3 inches (2.54×7.62 centimeters) were cut from each sheet. The film was then peeled away from the paper backing of each sample and folded into a U-shape with both sides of equal length.

The two arms of the "U" were compressed with a binder clip to from a loop at the closed end of the "U". The edge of the clip closest to the loop was located about 0.5 inch (1.3 cm.) from the center of the loop.

The films were then heated and evaluated in accordance with the procedure described in ASTM test D 3291-92. Each sample was heated at 73° C. for 24 hours. Following heating the curved interior portion of the loop of each sample was daubed with a cigarette paper to determine whether any plasticizer had exuded from the polymer. The amount of exuded liquid was rated on a scale of from 0 (no liquid present), to 3 (surfaces of film and paper covered with a continuous layer of liquid exudate).

All of the films evaluated were rated "0" with the exception of the film prepared from formulation A of the preceding Table 4 that contained 55 parts by weight of the mixed ester plasticizer referred to in Table 1 as DEG3BL. This film sample was given a rating of "1", indicating only slight exudation with faint, discontinuous marks on the paper.

What is claimed is:

1. A liquid plastisol comprising
   A) particles of a dispersion grade polymer selected from the group consisting of homopolymers and copolymers of vinyl chloride, the particles having an average size of less than 10 microns;
   B) from 10 to 100 weight percent, based on the weight of said polymer, of a plasticizer composition comprising
   1) a diester corresponding to formula (I)

$$R^1C(O)OR^2O(C))CR^3; \quad \text{I}$$

2) a diester corresponding to formula (II)

$$R^1C(O)OR^2O(O)CR^1; \text{ and} \quad \text{II}$$

3) a diester corresponding to formula (III)

$$R^3C(O)OR^2O(O)CR^3 \quad \text{III}$$

wherein $R^1$ is at least one radical selected from the group consisting of phenyl and alkyl-substituted phenyl, $R^2$ is a divalent radical of the formula $—R^4(OR^4)—$, $R^3$ is an alkyl radical containing from 3 to 21 carbon atoms, $R^4$ is an alkyl radical containing m 2 to 4 carbon atoms, m represents 0 or the integer 1 or 2 and the molar ratio of $R^1$ to $R^3$ radicals is from 3:1 to 12:1, and
   C) at least one monoester exhibiting a formula selected from the group consisting of $R^1C(O)OR^2OH$ and $R^3C(O)OR^2OH$ and said monoester constitutes up 5 weight percent of said plasticizer composition.

2. A plastisol according to claim 1 wherein $R^1$ is phenyl, m is 1 or 2 and $R^3$ contains from 8 to 16 carbon atoms.

3. A plastisol according to claim 2 wherein $R^4$ is ethyl or propyl and $R^3$ contains 11 carbon atoms.

4. A plastisol according to claim 1 wherein said plastisol additionally comprises at least one ester derived from a monohydric alcohol and a carboxylic acid a plasticizer for said polymer.

5. A plastisol according to claim 4 wherein said carboxylic acid is selected from the group consisting of benzoic acid, phthalic acid and adipic acid.

* * * * *